United States Patent
Keller

(10) Patent No.: US 7,559,950 B2
(45) Date of Patent: Jul. 14, 2009

(54) HIP PROSTHESIS INCLUDING A SHAFT TO BE FIXED IN THE MEDULLARY CANAL OF THE FEMUR

(75) Inventor: Arnold Keller, Kayhude (DE)

(73) Assignee: Waldemar Link GmbH & Co. KG, Hamburg (DE)

( * ) Notice: Subject to any disclaimer, the term of this patent is extended or adjusted under 35 U.S.C. 154(b) by 91 days.

(21) Appl. No.: 10/541,372

(22) PCT Filed: Jan. 14, 2004

(86) PCT No.: PCT/EP2004/000224

§ 371 (c)(1),
(2), (4) Date: Jul. 5, 2005

(87) PCT Pub. No.: WO2004/064688

PCT Pub. Date: Aug. 5, 2004

(65) Prior Publication Data

US 2006/0041316 A1 Feb. 23, 2006

(30) Foreign Application Priority Data

Jan. 17, 2003 (EP) .................................. 03001040
Jul. 16, 2003 (EP) .................................. 03016156

(51) Int. Cl.
*A61F 2/32* (2006.01)
(52) U.S. Cl. .................................................. 623/23.31
(58) Field of Classification Search ..... 623/22.11–22.2, 623/23.14, 23.15, 23.17, 23.21, 23.26, 23.44
See application file for complete search history.

(56) References Cited

U.S. PATENT DOCUMENTS

| | | | |
|---|---|---|---|
| 2,719,522 A | 10/1955 | Hudack | |
| 3,067,740 A | 12/1962 | Haboush | |
| 4,141,088 A * | 2/1979 | Treace et al. | 623/22.41 |
| 4,261,063 A * | 4/1981 | Blanquaert | 623/23.46 |
| 4,279,042 A * | 7/1981 | Andriacchi et al. | 623/23.15 |
| 4,495,664 A * | 1/1985 | Blanquaert | 623/23.36 |
| 4,530,116 A | 7/1985 | Frey | 623/23.29 |
| 4,549,319 A * | 10/1985 | Meyer | 623/23.23 |
| 4,623,349 A * | 11/1986 | Lord | 623/23.44 |
| 4,664,668 A | 5/1987 | Beck et al. | |
| 4,714,470 A * | 12/1987 | Webb et al. | 623/23.44 |

(Continued)

FOREIGN PATENT DOCUMENTS

DE           2839092           3/1980

(Continued)

OTHER PUBLICATIONS

International Preliminary Report on Patentability directed to counterpart PCT/EP2004//000224.

*Primary Examiner*—David J Isabella
*Assistant Examiner*—Ann Schillinger
(74) *Attorney, Agent, or Firm*—Morrison & Foerster LLP

(57) ABSTRACT

A hip prosthesis includes a shaft which is configured to be anchored in the medullary canal of a femur and whose distal portion, which is to be anchored in the diaphysis, has a core cross-section which tapers toward the distal end and which, at least on the lateral side and medial side, has longitudinal ribs whose height increases from proximal to distal.

11 Claims, 1 Drawing Sheet

U.S. PATENT DOCUMENTS

| | | | |
|---|---|---|---|
| 4,728,334 A | 3/1988 | Spotorno | |
| 4,784,124 A * | 11/1988 | Kaltenbrunner et al. | 606/63 |
| 4,938,773 A * | 7/1990 | Strand | 623/23.15 |
| 5,002,580 A * | 3/1991 | Noble et al. | 623/23.23 |
| 5,108,453 A * | 4/1992 | Kotz et al. | 623/23.29 |
| 5,156,627 A | 10/1992 | Amstutz et al. | |
| 5,480,452 A * | 1/1996 | Hofmann et al. | 623/23.28 |
| 5,507,833 A * | 4/1996 | Bohn | 623/23.3 |
| 5,593,446 A * | 1/1997 | Kuoni | 623/23.44 |
| 5,607,607 A * | 3/1997 | Naiman et al. | 219/121.68 |
| 5,645,740 A * | 7/1997 | Naiman et al. | 219/121.68 |
| 5,935,172 A * | 8/1999 | Ochoa et al. | 623/23.36 |
| 6,030,417 A * | 2/2000 | Bresler et al. | 623/23.15 |
| 6,190,416 B1 * | 2/2001 | Choteau et al. | 623/22.12 |
| 6,436,148 B1 | 8/2002 | DeCarlo, Jr. et al. | |
| 6,702,854 B1 * | 3/2004 | Cheal et al. | 623/22.42 |
| 6,770,100 B2 * | 8/2004 | Draenert | 623/23.26 |
| 7,044,975 B2 * | 5/2006 | Cheal et al. | 623/22.42 |
| 2002/0045950 A1 * | 4/2002 | Draenert | 623/23.26 |
| 2004/0010319 A1 * | 1/2004 | McTighe et al. | 623/23.21 |
| 2004/0107001 A1 * | 6/2004 | Cheal et al. | 623/22.42 |
| 2004/0236430 A1 * | 11/2004 | Koch et al. | 623/23.31 |

FOREIGN PATENT DOCUMENTS

| | | |
|---|---|---|
| DE | 29907259 | 9/1999 |
| EP | 238860 | 1/1985 |
| EP | 649642 | 10/1993 |
| EP | 845251 | 10/1993 |
| EP | 682924 | 2/1995 |
| EP | 677281 | 3/1995 |
| EP | 0623321 | 1/1997 |
| EP | 0821923 | 2/1998 |
| EP | 1044665 | 4/2000 |
| FR | 2549718 | 7/1983 |
| FR | 2686789 | 1/1992 |
| FR | 2791252 | 3/1999 |
| GB | 2203943 | 4/1987 |
| JP | 61-56641 | 3/1986 |
| JP | 64-25851 | 1/1989 |
| JP | 2000-93440 | 4/2000 |
| WO | WO-02/100302 | 12/2002 |

* cited by examiner

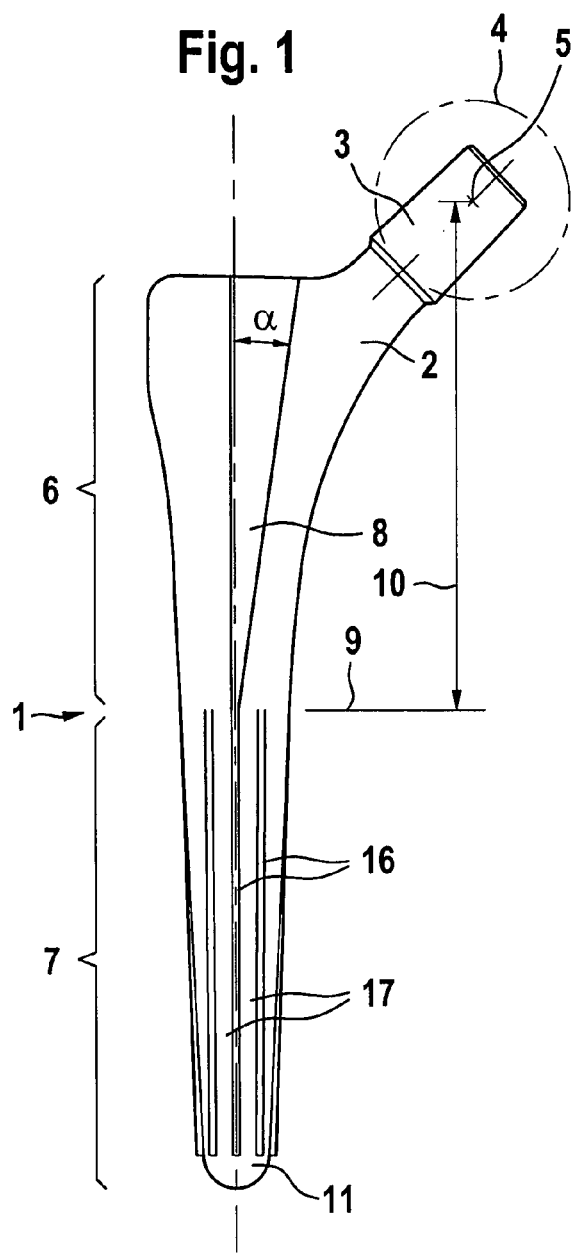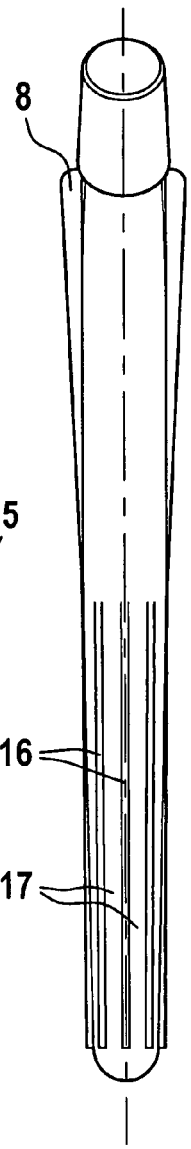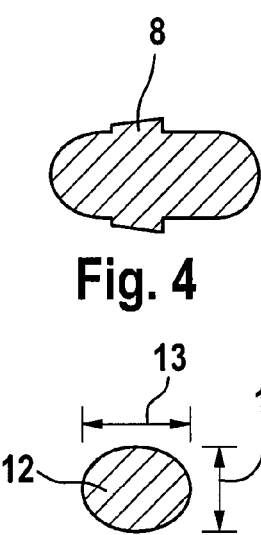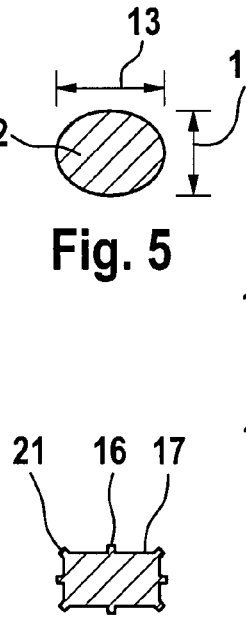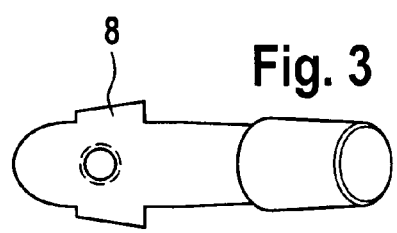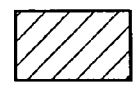

HIP PROSTHESIS INCLUDING A SHAFT TO BE FIXED IN THE MEDULLARY CANAL OF THE FEMUR

FIELD AND BACKGROUND OF THE INVENTION

The diaphysis of the femur, i.e. the elongate part of this bone beginning at the lesser trochanter, has a relatively thick and strong cortex (cortical substance) and is therefore especially suitable for anchoring of a prosthesis shaft. Prostheses are known which exploit this fact in that their shaft extending into the diaphysis of the femur has a shaft cross-section which is adapted to the size of the medullary canal and has an approximately constant cross-section (U.S. Pat. No. 4,549,319, DE-A-2839092). It is true that there are also prostheses whose shaft cross-section tapers toward the end in the distal portion (EP-A-135755, U.S. Pat. No. 2,719,522, U.S. Pat. No. 3,067,740). However, these are either prostheses which are anchored with cement and whose cross-sectional difference from the medullary canal is therefore not important (Schneider: Die Totalprothese der Hüfte [The total hip prosthesis], page 120), or prostheses in which the shaft is intended to wedge itself in the medullary cavity by virtue of its wedge shape (Müller, loc. cit., page 214 et seq.). The latter have the disadvantage that the wedging leads to a high concentration of force at the wedge positions. However, a cementless force transmission is desired that covers a large surface area, but, based on previous experience, this requires individual adaptation of the prosthesis shaft to the shape of the medullary canal and, because of the very high costs involved, is normally not considered. They are also insufficiently secured-against twisting.

SUMMARY OF THE INVENTION

It is therefore an object of the invention to make available a hip prosthesis whose shaft, in cementless implantation, is able to permit force transmission across a large surface area in the diaphyseal area while at the same time being secure against twisting.

The solution according to the invention lies in the features of as disclosed below. In particular, the invention is a hip prosthesis that includes a shaft which is configured to be anchored in the medullary canal of the a femur and has a distal portion which is configured to be anchored in the diaphysis. The shaft has a core cross-section which tapers toward the distal end of the shaft and has longitudinal ribs on the lateral and medial sides whose height increases from a proximal portion of the shaft to a distal end portion of the shaft. The shaft core cross-section at a distance of 1 cm from the distal end portion being substantially rectangular, with an axis ratio of at least 1:4 or, in some embodiments, at least 1:5. Near its distal end at least, the shaft has a rib on each of its two lateral edges, the height of which is on average under 2 mm, the boundary of the shaft core cross-section between the two ribs located on the lateral edges not protruding further laterally from the prosthesis than the two ribs located on the lateral edges. A rib may also be provided between the two ribs located on the lateral edges that protrudes from the prosthesis by not more than 2 mm further laterally than these two ribs. The shaft may also include ribs provided on each of the medial edges. Where a rib is provided between the rib on the lateral and medial edges, it preferably protrudes not more than 2 mm in the a ventral or dorsal direction from the prosthesis than the ribs arranged on the lateral and medial edges. The ribs may be rough.

The shaft may have a core cross-section that tapers on average at least 8 mm$^2$/cm of length, preferably over 10 mm$^2$/cm of length, along a length of the shaft of at least 4 cm. The prosthesis has a reduction in cross-sectional dimension in the latero-medial direction of the distal shaft portion along a length of at least 4 cm of the distal shaft portion of on average at least 0.5 mm/cm of length, preferably more than 0.8 mm/cm of length. The rib height may increase from the proximal end of the distal portion to its distal end by an amount of from less than 0.5 mm to 0.5 to 1.5 mm.

Accordingly, the distal portion of the shaft, which is to be anchored in the diaphysis, has a core cross-section which tapers toward the end and which, at least on the lateral side and medial side, has longitudinal ribs whose height above the surface of the shaft core increases from proximal to distal. The desired force transmission across a large surface area is brought about by the fact that, when the shaft is driven into the medullary canal, the surfaces formed by the shaft core and increasing in a wedge shape between the ribs lead to a compaction of the lamellar bone substance present there, which is thus held securely between the ribs. A known shaft with a closed, rib-free surface and with a lack of adaptation of its shape to the medullary canal, even when it thickens in a wedge shape, affords only very few and small contact surfaces at which force transmission can take place, because it can escape sideways. By contrast, the shaft according to the invention is guided by the ribs during its insertion, so that it cannot escape sideways, and additional force transmission areas are created by the pushing-together and compression of bone substance between the ribs. Even though the amount of bone material to be compressed and its local arrangement may differ from one case to another, a good force transmission is in this way created, in any case in some areas, from the shaft and through the compressed bone substance to the hard cortical bone. This results not only in good initial strength, but also affords the possibility of subsequent growth of new bone substance into the remaining interstices and, consequently, ideal conditions for a good long-term fit of the prosthesis. This does not rule out the prosthesis also being designed for force transmission in its proximal area. The distal configuration according to the invention is even particularly suitable for cases in which the prosthesis also has proximal force transmission means.

Where known shafts are provided with ribs, they do not permit the compression effect according to the invention. In a known prosthesis (U.S. Pat. No. 2,719,522) with ribs extending in the circumferential direction, these ribs shave off lamellar bone substance from the surface of the medullary space without compressing it. In another known prosthesis (U.S. Pat. No. 3,067,740), the shaft is provided at intervals with a protruding collar whose purpose is to shave off bone substance from the surface of the medullary space and pack it around ribs on the shaft while the latter is being driven into the bone. This is intended to promote callus formation. However, since the sharp collars protrude much further than the ribs, they instead have the effect, in their prominent transmission of force onto the bone, of cutting into the latter and thereby damaging it. In other known prostheses (DE-U-29907259; DE-C-4315143; EP-B-677281; EP-B-821923), a shaft is ribbed in the longitudinal direction. It does not taper between the ribs (i.e. the height difference between the shaft core surface and the ribs does not increase from proximal to distal) and cannot therefore provide sufficient compression. This applies also to the shaft of another known prosthesis (EP-B-682924) in which the height of the ribs above the surface of the shaft core cross-section decreases in stages.

To ensure that the bone substance compressed by the conical shaft core is secured safely between the ribs, at least three ribs should be present on each of the laterally and medially directed surface portions of the core. In addition, longitudinal ribs are expediently also present on the front face and rear face.

For effective compression of the bone substance, it has proven useful to provide a tapering of the core cross-section toward its end which, along a length of at least 4 cm, is on average at least 8 mm$^2$/cm of length, and preferably over 10 mm$^2$/cm. It should not exceed 20 mm$^2$/cm and should preferably be below 16 mm$^2$/cm on average.

In the latero-medial (hereinafter abbreviated "LM") plane, the tapering of the core size along a length of 4 cm should be at least 0.5 mm/cm, and preferably approximately 1 mm/cm.

The rib height does not have to be great. It should on average be under 2 mm. An average rib height of 1 mm and less is generally sufficient. A shaft design is expedient in which the rib height increases from the proximal end of the distal portion to its distal end from 0 to 0.5 mm to 1.5 mm, preferably approximately 1 mm.

Since the core cross-section is mainly responsible for the compression of the bone substance, and the ribs only have a holding and guiding function, the extent of their cross-section should remain small. The average extent of their cross-section in the circumferential direction should not be greater than 30% of their center distance and for example should be of the order of 20%. The determination of their cross-section is based on their height between the surface of the core cross-section and their tip. Apart from the ribs, there should be no other projections in the ribbed part of the shaft. If, however, any additional projections are present, these should not protrude any further than the ribs.

The length of the ribbed, distal shaft portion is expediently at least 4 cm and preferably approximately 5 to 8 cm. A condition here is that the proximal start of the distal shaft portion lies approximately 7 to 9 cm below the height of the joint head.

In the area where they have their greatest height, the flanks of the ribs enclose an angle of preferably not more than 30° with the radius through the rib center. It is further preferable for this angle to be less than 20°. An exception to this rule may apply when the shaft, at the time of its production, has to be demolded transverse to its longitudinal direction. In relation to the demolding direction (which is generally the direction transverse to the plane in which the main extent of the prosthesis lies), the ribs should not be undercut in this case.

In the upper and middle area, i.e. also at the proximal end of the distal, ribbed shaft portion, the shaft expediently has an oval or elongate cross-section whose longer axis lies in the latero-medial plane. At the distal end, the core of the distal portion is expediently circular in cross-section, so that it merges along its length from the oval cross section to the circular cross section. The axis ratio at its proximal end should be at least 1:2.

In another embodiment, the ribbed portion of the shaft has an elongate rectangular cross-section with the longer axis in the LM direction, the axis ratio being at least 1.4 to 1. At the distal end, where the cross section is measured at a distance of 1 cm from the end to take into account the possible presence of a rounded end, the axis ratio is at least 1.5 to 1. In this case, a rib should be provided at least on each of the two lateral edges, since the guiding task assigned to the ribs is especially important at this location. To ensure that neither of these edges is prevented from coming into guiding contact with the boundary of the medullary canal by other projecting parts of the shaft, the shaft core cross-section between the two ribs located on the lateral edges should not protrude further laterally than these. If there is a further lateral rib present between the two ribs located on the lateral edges, this further rib should protrude not more than 2 mm, preferably not more than 1 mm, further laterally than these.

A rib can also be provided on each of the medial edges. In this connection, it is expedient if, on the ventral and dorsal faces of the shaft cross-section, the shaft core cross-section between the ribs, which are assigned to the lateral and medial edges delimiting this side, protrude not more than 1 mm in the ventral or dorsal direction beyond these. If one or more ribs are also provided on this side between the edges, they should protrude not more than 2 mm, preferably not more than 1 mm, in the ventral or dorsal direction than the ribs provided on the edges.

So that the ribs can more easily perform their guiding task, they should, according to a further feature of the invention, be made rough in order to more easily cut into the hard cortical bone. To avoid undesirably excessive damage to the bone, this roughness should not be too coarse. The center distance between adjacent grains or teeth should not exceed 0.5 mm and is expediently of the order of 0.1 mm on average.

BRIEF DESCRIPTION OF THE DRAWINGS

The invention is explained in more detail below with reference to the drawing which depicts an advantageous illustrative embodiment of the prosthesis. In the drawing:

FIG. 1 shows a view from the front,

FIG. 2 shows a view from the medial direction,

FIG. 3 shows a view from above,

FIGS. 4 to 6 show sections through the shaft at different heights thereof, with FIG. 4 being drawn transversely in the region of reference numeral 2 on FIG. 1, FIG. 5 being drawn transversely in the region of reference numeral 9 on FIG. 1 and FIG. 6 being drawn transversely in the region of reference numeral 17 on FIG. 1, and FIG. 7 shows a section, corresponding to FIG. 5, of the embodiment with a rectangular shaft core cross-section.

DETAILED DESCRIPTION OF THE INVENTION

The prosthesis is made up of a shaft 1, a neck 2 and a cone 3 for attachment of a joint head 4 whose circumference is indicated by a dot-and-dash line and which has a center point 5. This is a so-called straight shaft prosthesis. In this known type of prosthesis, the shaft is substantially straight in its entirety. In contrast to prostheses whose shaft is curved in the proximal area so that their direction equates to the direction of the neck 2, this prosthesis is introduced in only one direction into the hollow created for receiving it in the bone. The shaft is made up of a proximal portion 6 and a distal portion 7. The proximal portion can be equipped with special means for improved force transmission to the bone substance surrounding the shaft in the epiphyseal area of the femur. In concrete terms, this is achieved with a pair of ribs 8. The shaft cross-section is elongate in the LM direction in this area, as is shown in FIGS. 4 and 5 and in FIG. 7.

The transition area 9 between the proximal portion and the distal portion of the shaft is arranged such that, in the implanted state, it comes to lie slightly below the lesser trochanter, and the distal shaft portion 7 accordingly lies in an area of the medullary canal in which this is delimited by a thick cortical bone, from which some lamellar bone substance extends into the medullary canal. The transition area does not have to be specifically marked on the prosthesis. It can be recognized from the fact that it lies where, in the implanted state, the lesser trochanter is approximately located, or more precisely the lower margin thereof. It lies about 7 to 9 cm deeper than the center point 5 of the joint head, measured according to the arrow 10 in the shaft direction.

Below the transition area 9, the distal shaft portion 7 has a length of approximately 4 to 8, preferably approximately 6 to 7 cm. Its core 12 tapers from its proximal end 9 to its distal end 11 in a ratio of approximately 10 to 15 mm$^2$/cm. The tapering takes place principally on the lateral and medial sides. The LM dimension 13 at the upper end 9 of the distal portion, which dimension is approximately 17 mm, decreases as far as the distal end 11, according to FIG. 6, to approximately 14 mm.

In the distal portion, the surface of the shaft core is equipped with ribs 16 which between them enclose surface strips 17 of the shaft core surface. The ribs arranged on the longitudinal edges of the rectangular cross section are indicated in FIG. 6 by reference numeral 21. At the transition 9, the ribs 16 merge with zero height into the shaft surface, and at the distal end 11 they reach a height of approximately 1 mm above the shaft core surface. On account of the reduction in cross section of the shaft core from proximal to distal, the surface strips 17 formed between the ribs act as wedge surfaces which, when the shaft is driven into the medullary canal, compress the predominantly lamellar bone substance located there in the interspace between the surface of the shaft core and the cortical boundary of the medullary space. The bone substance cannot be squeezed off to the sides and escape, because it is held securely by the ribs 16. In this way, strong and compact force transmission bridges are created between the prosthesis shaft and the cortical boundary of the medullary space, even in those areas of the shaft cross section which, without this compression, would not reach the cortical boundary of the medullary space and would therefore not be able to take part in the force transmission. Since the decrease in the shaft cross-sectional dimension is greater in the LM direction than in the AP direction, the strongest compression takes place on the lateral and medial flanks of the shaft. The most effective force transmission bridges will also therefore be formed there by compression of bone substance. This is advantageous in view of the fact that most of the forces have to be transmitted in this direction between prosthesis shaft and bone. However, a wedge shape is also present on the anterior and posterior faces of the shaft and can bring about a corresponding effect there.

If a rasp or suchlike instrument is used to prepare the bone cavity in which the prosthesis shaft is to be fitted, the cross-sectional dimension of said rasp or instrument, in its part corresponding to the ribbed portion of the prosthesis shaft, should not be greater than that of the core of the prosthesis shaft, so that bone substance is preserved which can be compressed between the surface of the shaft core and the inner face of the hard cortical bone.

The shaft core has, at least near its distal end, a rectangular shaft cross-section. The ribs 21 arranged on the longitudinal edges perform a particularly pronounced guidance function because of their position. Even if a shaft portion were to lie eccentrically offset in the ventral or dorsal direction in the medullary canal, it can be assumed that, in the distal portion, a rib located on a lateral edge will come into engagement with the surface of the medullary space. To ensure that this is also the case with a particularly unfavorable position of the shaft or an unfavorable shape of the cross-section of the medullary space, according to the invention the ribs provided on the lateral edges should also be prominent compared to the rest of the lateral surfaces of the shaft cross-section, as has been indicated above. The same applies to the relationship of the lateral edge ribs to the ventral and dorsal surface parts of the shaft.

The invention claimed is:

1. A hip prosthesis, comprising:
   a shaft which is configured to be anchored in a medullary canal of a femur and includes a distal portion which is configured to be anchored in a diaphysis,
   the shaft having a core cross-section which tapers toward a distal end, the shaft core cross-section being substantially rectangular with an axis ratio of at least 1.5:1 at a distance of approximately 1 cm from the distal end,
   the distal portion of the shaft extending from a proximal start of the shaft to the distal end;
   wherein the distal portion of the shaft comprises a plurality of longitudinal ribs protruding from the shaft and arranged on a lateral side and a medial side of the distal portion of the shaft, the plurality of longitudinal ribs including at least two edge ribs arranged on lateral corners of the rectangular cross-section of the shaft near the distal end,
   wherein a height of the plurality of ribs continuously increases relative to the shaft core surface from the proximal start of the distal portion to the distal end of the shaft, whereas a height of the plurality of ribs does not increase relative to a longitudinal axis of the shaft from the proximal start of the distal portion to the distal end of the shaft.

2. The prosthesis as claimed in claim 1, further comprising a side rib provided between the two edge ribs located on the lateral corners that protrudes from the prosthesis by no more than 2 mm further laterally from the shaft than the two ribs located on the lateral corners.

3. The prosthesis as claimed in claim 2, further comprising two additional edge ribs provided on medial corners of the rectangular cross-section of the shaft.

4. The prosthesis as claimed in claim 3 further comprising an additional side rib provided between one of the edge ribs provided on the lateral corners and one of the additional edge ribs located on the medial corners that protrudes by no more than 2 mm in a ventral or dorsal direction from the shaft than the respective edge rib and addition rib.

5. The prosthesis as claimed in claim 1 or 2, wherein a shaft core cross-section at the proximal end is substantially rectangular with an axis ratio of at least 1.4:1.

6. The prosthesis as claimed in claim 1 or 2, wherein the ribs have roughened surfaces.

7. The prosthesis as claimed in claim 1 or 2, wherein a tapering of the core cross-section along a length of at least 4 cm is on average at least 8 mm$^2$/cm of length.

8. The prosthesis as claimed in claim 7, wherein a tapering of the core cross-section along a length of at least 4 cm is on average over 10 mm$^2$/cm of length.

9. The prosthesis as claimed in claim 1 or 2, wherein a reduction in cross-sectional dimension in a latero-medial direction of the distal shaft portion along a length of at least 4 cm of the distal shaft portion is on average at least 0.5 mm/cm of length.

10. The prosthesis as claimed in claim 9, wherein a reduction in cross-sectional dimension in a latero-medial direction of the distal shaft portion along a length of at least 4 cm of the distal shaft portion is on average more than 0.8 mm/cm of length.

11. The prosthesis as claimed in claim 1 or 2, wherein the rib height increases from the proximal end of the distal portion to the distal end of the distal portion from less than 0.5 mm to 0.5 to 1.5 mm.

* * * * *